United States Patent
Hughes et al.

(10) Patent No.: US 8,733,005 B2
(45) Date of Patent: May 27, 2014

(54) DISPLAY DEVICE, KIT AND ASSEMBLY

(75) Inventors: Adrienne Hughes, New Paltz, NY (US); Jeffrey Magsitza, Pomona, NY (US); Kelly Law, Shung Shui (HK)

(73) Assignee: Adrienne Hughes, New Paltz, NY (US)

( * ) Notice: Subject to any disclaimer, the term of this patent is extended or adjusted under 35 U.S.C. 154(b) by 8 days.

(21) Appl. No.: 13/190,027

(22) Filed: Jul. 25, 2011

(65) Prior Publication Data
US 2012/0266511 A1    Oct. 25, 2012

Related U.S. Application Data

(60) Provisional application No. 61/478,227, filed on Apr. 22, 2011.

(51) Int. Cl.
*G09F 1/12* (2006.01)
(52) U.S. Cl.
USPC ............. 40/800; 40/124.07; 40/409; 40/738; 428/11
(58) Field of Classification Search
USPC ............... 281/22; 434/273, 86–92, 262, 266; 40/738, 743, 790, 791
See application file for complete search history.

(56) References Cited

U.S. PATENT DOCUMENTS

| | | | | |
|---|---|---|---|---|
| 2,324,277 | A * | 7/1943 | Casey et al. | 40/327 |
| 3,333,358 | A * | 8/1967 | Green et al. | 40/738 |
| 3,596,391 | A * | 8/1971 | Knight, Jr. | 40/720 |
| 3,624,939 | A * | 12/1971 | Gossard | 40/721 |
| 4,018,536 | A * | 4/1977 | Brenner | 401/292 |
| 4,022,318 | A * | 5/1977 | Goodman | 206/223 |
| 4,173,667 | A * | 11/1979 | Rusch | 428/11 |
| 4,224,364 | A * | 9/1980 | Hunt | 428/11 |
| 4,837,958 | A * | 6/1989 | Radovich | 40/538 |
| 5,251,943 | A * | 10/1993 | Dalbo et al. | 294/212 |
| 5,254,026 | A * | 10/1993 | Kaiser | 446/220 |
| 5,407,711 | A * | 4/1995 | Lovison et al. | 428/13 |
| 5,617,663 | A * | 4/1997 | Miki et al. | 40/738 |
| 5,619,816 | A * | 4/1997 | Ellison | 40/738 |
| 5,688,198 | A * | 11/1997 | Teifert et al. | 473/598 |
| 5,712,005 | A * | 1/1998 | Monn | 428/34.1 |
| 5,853,824 | A * | 12/1998 | Liu | 428/11 |

(Continued)

OTHER PUBLICATIONS

How to Make a Picture Snowglobe, Erin E. Clyburn, eHow.co.uk, downloaded Jan. 28, 2011, available at http://www.ehow.co.uk/print/how_6911822_make-picture-snowglobe.html (2 pages).

(Continued)

*Primary Examiner* — Shin Kim
(74) *Attorney, Agent, or Firm* — Gordon & Jacobson, PC

(57) ABSTRACT

A keepsake display device stores and displays a printed ultrasound image, and includes a substantially transparent convex hollow first member with a substantially closed smooth outer surface, a second member coupled to the first member to define a substantially closed outer surface for the device, and a display element adapted to receive the printed ultrasound image and display it through the outer surface of the first member. The first and second members can be shaped to mimic a pregnant belly and a woman's buttocks, together representing the midsection of a pregnant woman. A kit includes the display device plus one or more of a lamination member, a real or plastic birthstone or a set of real or plastic birthstones, a template useful for cutting the ultrasound image, and glue. An assembly includes the display device and a figurine such a stork which can hold the display device from its beak.

8 Claims, 8 Drawing Sheets

(56) References Cited

U.S. PATENT DOCUMENTS

| | | | |
|---|---|---|---|
| D430,394 S | 9/2000 | Rothschild | |
| D430,912 S * | 9/2000 | Hanna et al. | D21/714 |
| 6,203,562 B1 * | 3/2001 | Ohkubo | 606/204 |
| 6,217,956 B1 * | 4/2001 | Heidkamp | 428/11 |
| 6,293,038 B1 * | 9/2001 | Chang | 40/738 |
| 6,399,167 B1 * | 6/2002 | Lewis, Jr. | 428/11 |
| 6,438,878 B1 * | 8/2002 | Fine et al. | 40/409 |
| 6,907,683 B1 * | 6/2005 | Kronblad | 40/1.5 |
| 7,100,317 B1 * | 9/2006 | Strong | 40/124.07 |
| 7,117,621 B2 * | 10/2006 | Chang | 40/738 |
| D565,458 S | 4/2008 | Jordan | |
| 7,421,810 B2 * | 9/2008 | Schymura | 40/738 |
| 7,430,823 B1 * | 10/2008 | Chung | 40/409 |
| 7,464,480 B2 * | 12/2008 | Vetromila | 33/436 |
| 7,596,896 B2 * | 10/2009 | Crowell et al. | 40/124.07 |
| D621,455 S * | 8/2010 | Chernick et al. | D21/713 |
| D633,568 S * | 3/2011 | Hill et al. | D20/10 |
| 7,954,669 B2 * | 6/2011 | VanGordon et al. | 222/78 |
| D644,460 S * | 9/2011 | Lewis | D6/495 |
| 8,029,394 B2 * | 10/2011 | Burke | 473/594 |
| 8,172,708 B2 * | 5/2012 | Burke | 473/594 |
| 8,215,041 B2 * | 7/2012 | Hill | 40/603 |
| 2003/0160824 A1 * | 8/2003 | Szumla | 345/769 |
| 2006/0010913 A1 * | 1/2006 | Torres et al. | 63/23 |
| 2006/0248760 A1 * | 11/2006 | Brenner | 40/490 |
| 2006/0248764 A1 * | 11/2006 | Spiegelberg | 40/594 |
| 2007/0125682 A1 * | 6/2007 | Requate | 206/575 |
| 2008/0263915 A1 * | 10/2008 | Wardell | 40/1 |
| 2009/0050505 A1 * | 2/2009 | Rubin | 206/459.5 |
| 2009/0315211 A1 * | 12/2009 | England | 264/222 |
| 2012/0227298 A1 * | 9/2012 | Alicea | 40/610 |

OTHER PUBLICATIONS

Photo Snow Globe for 2×3 Inch Photos, Amazon.com, downloaded Jan. 28, 2011, available at http://www.amazon.com/Photo-Snow-Globe-Inch-Photos/dp/B000EJ1950 (6 pages).

This Snow Globe Has a Dry Center Slot for Photos or Other Decorations (Lot/3), Amazon.com, downloaded Jan. 28, 2011 (5 pages).

* cited by examiner

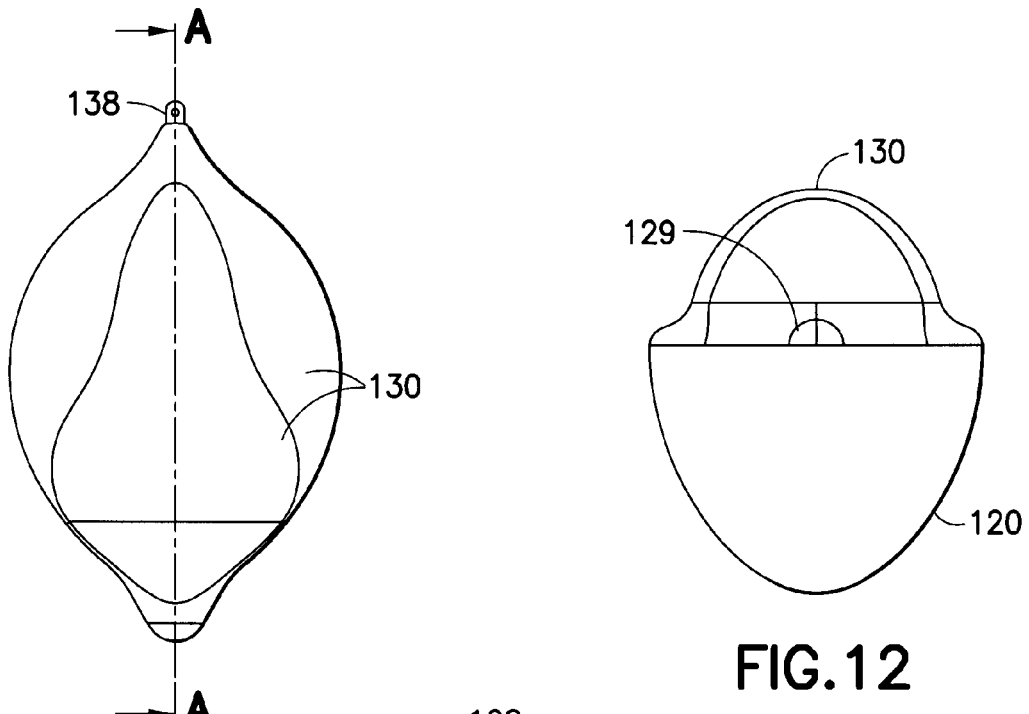
FIG.11
FIG.12
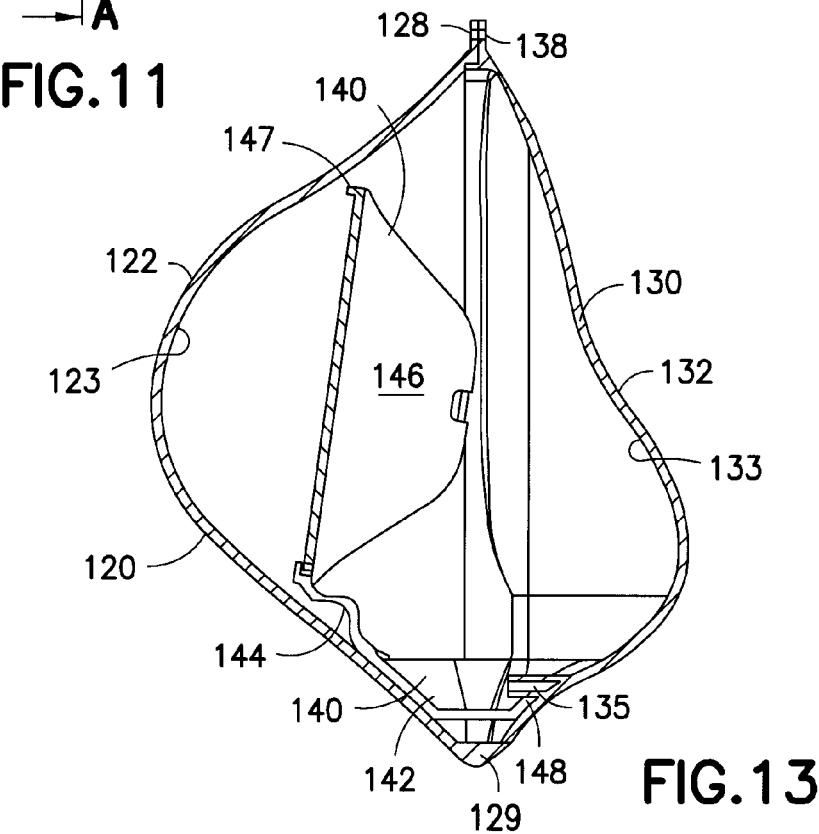
FIG.13

DISPLAY DEVICE, KIT AND ASSEMBLY

CROSS-REFERENCE TO RELATED APPLICATIONS

This application claims priority from provisional application U.S. Ser. No. 61/478,227 filed on Apr. 22, 2011 which is hereby incorporated by reference.

BACKGROUND OF THE INVENTION

1. Field of the Invention

The present invention relates to a picture display device, kit and assembly. More particularly, the present invention relates to a kit and display device for an ultrasound image of an unborn child, and an assembly that includes the display device and a stand.

2. State of the Art

It is now commonplace for obstetricians to take ultrasound images of fetuses in utero. Often, the expectant mother or parents are provided by the doctor with a printed image which can be treated as a keepsake. The image is typically printed on a thin piece of thermal paper that has a tendency to curl.

SUMMARY OF THE INVENTION

A keepsake ornamental display device is provided for safely storing and displaying a printed ultrasound image. The display device includes a substantially transparent convex first member with a preferably smooth surface which in one embodiment mimics a pregnant belly. A second member is provided to close the back of the convex member. The second member may take any of various shapes. In one embodiment, the second member is shaped so that together, the first member and second member represent the midsection of a pregnant women. The second member is optionally more opaque than the first member.

In one embodiment, one or more tracks adapted to receive a laminated printed ultrasound image are located on the inside surface of the convex member. If desired, two parallel tracks can be provided and adapted to receive a rectangular laminated picture. With parallel tracks, the laminated picture can be slid into place.

In another embodiment, the second member includes a surface which extends inside the convex member, and one or more tracks may be provided on the outside surface of the second member instead of being forming on the inside of the convex member.

In another embodiment, a third member is provided to sit between the first and second members. The third member is provided to capture and/or support the laminated printed ultrasound image. The third member may be provided with one or more tracks or edges which hold the laminated printed ultrasound image in place.

In one embodiment, a kit includes the first member and second member and a lamination member. The printed ultrasound image can be placed inside the lamination member to form a laminated structure that can be received in the tracks. The kit may also include such items as a template for expediting cutting of the printed ultrasound image, scissors, a birthstone, set of birthstones, or one or more plastic chips with the colors of the various birthstones, and cement or glue.

In different embodiments, the lamination member may be generally rectangular or generally oval. Where a generally oval lamination member is provided, the printed ultrasound image is preferably cut to the size of the oval lamination member.

When the display device is used as part of an assembly, one or both of the outer two members of the display device is preferably provided with an opening for receiving a ring or hook. A figurine, preferably resembling a stork is provided to hold the display device via the opening or via the ring or hook. More particularly, the figurine has a stand and a body extending from the stand, with a portion of the body adapted to extend through an opening, ring or hook so as to hold the display device in a dangling position above the horizontal level of the stand. Where the figurine is a stork, the body includes one or more legs attached to the stand, a main body area, and a head with a beak, with the beak adapted to extend through the opening, ring or hook.

Objects and advantages of the invention will be understood by reference to detailed description taken in conjunction with the drawings.

BRIEF DESCRIPTION OF THE DRAWINGS

FIG. 11 is a rear plan view of the second embodiment of FIG. 8.

FIG. 12 is a bottom plan view of the second embodiment of FIG. 8.

FIG. 13 is a cross-section through FIG. 11.

DETAILED DESCRIPTION OF THE PREFERRED EMBODIMENTS

Figure 1:
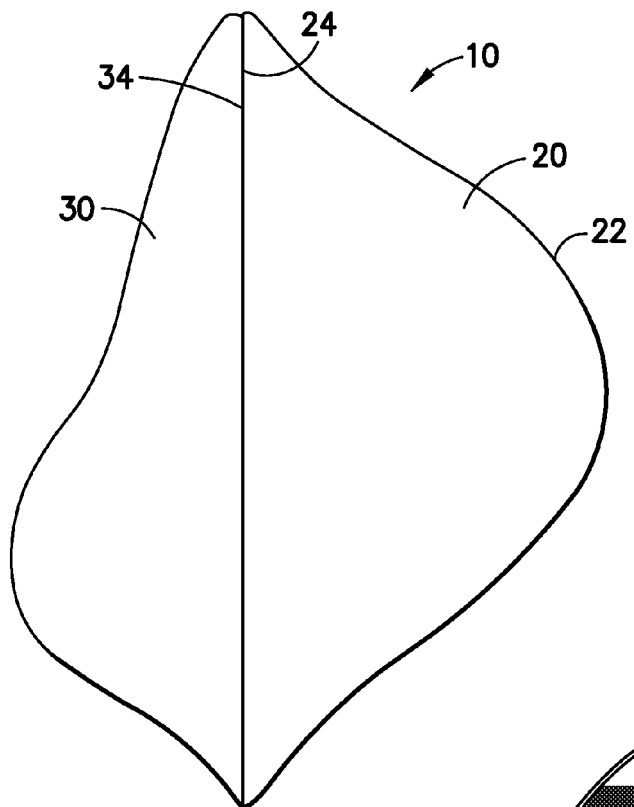
FIG. 1 is a side view of a first embodiment of a display device.
Figure 2:
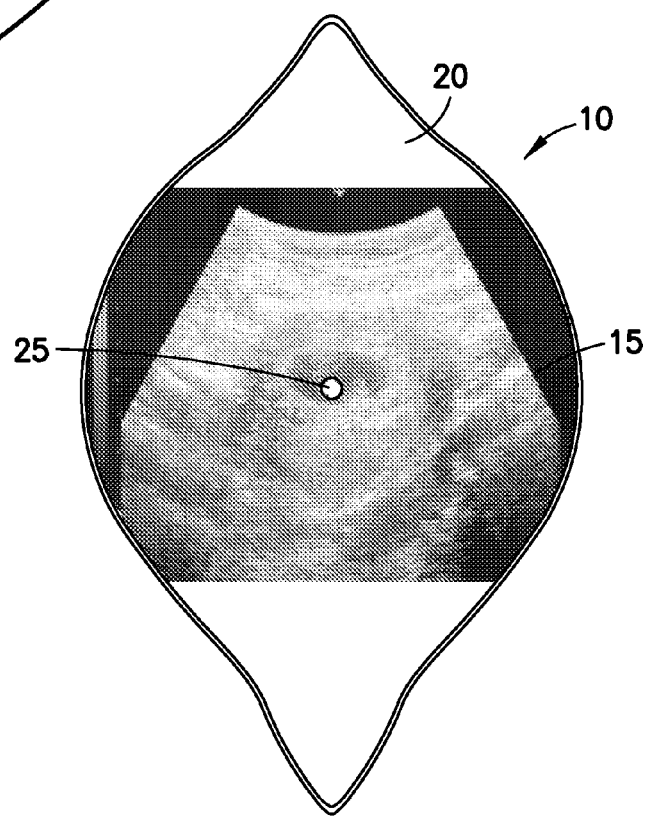
FIG. 2 is a front view of the first embodiment with a laminated picture located therein.
Figure 3:
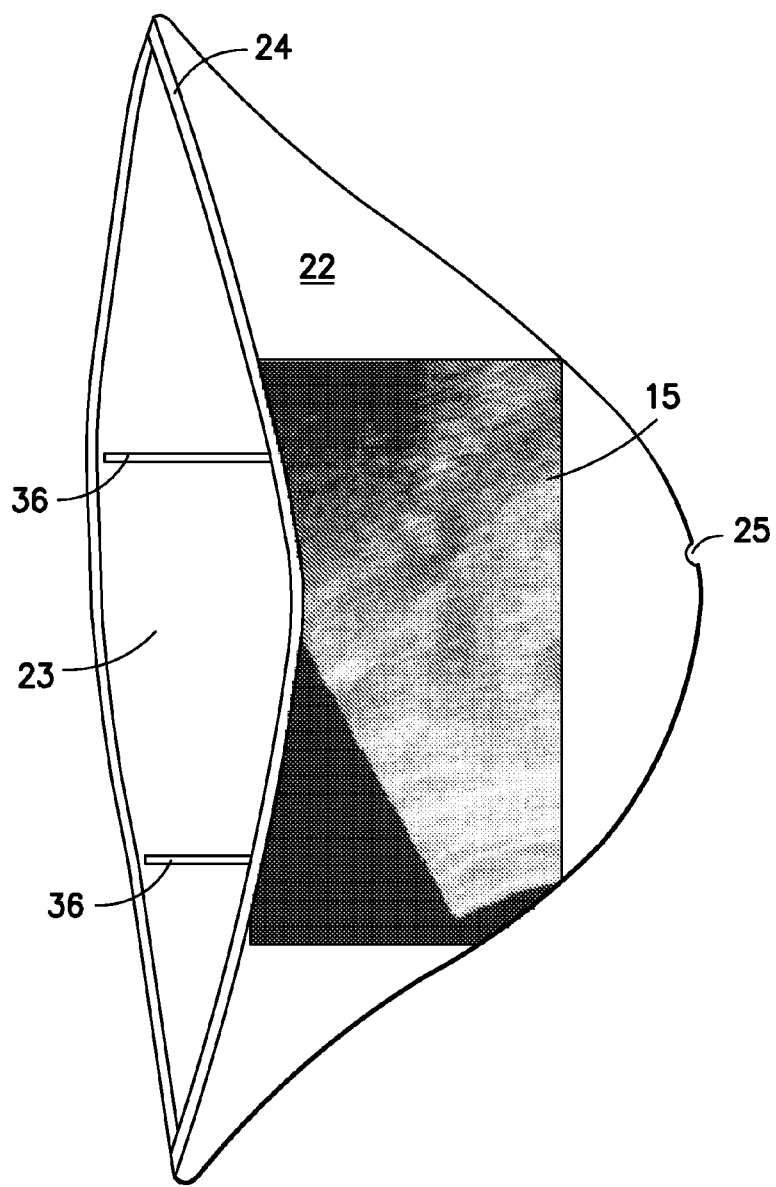
FIG. 3 is side perspective view of the front piece of the display device with the laminated picture located therein.
Figure 4:
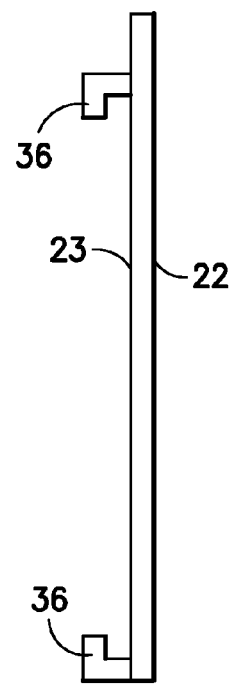
FIG. 4 a detailed view of the track seen in FIG. 3.
Figure 5:
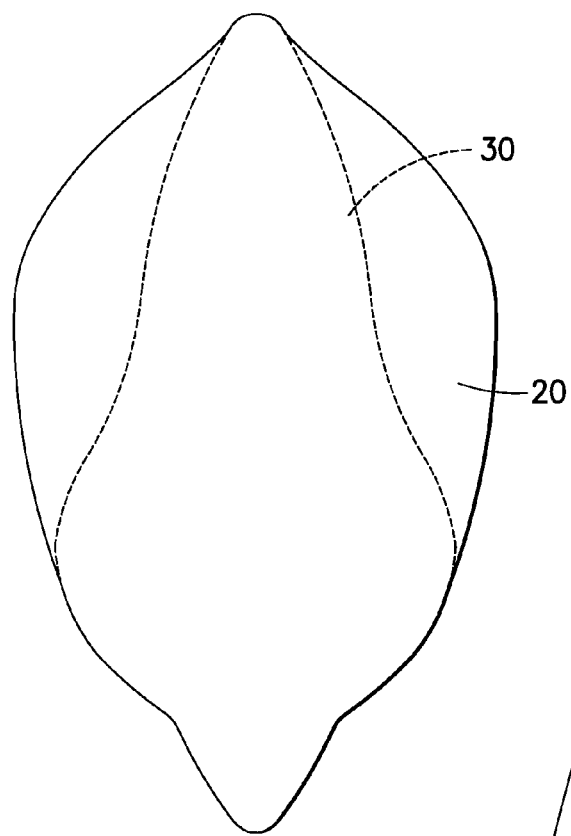
FIG. 5 is a plan view of the rear piece of the first embodiment.
Figure 6:
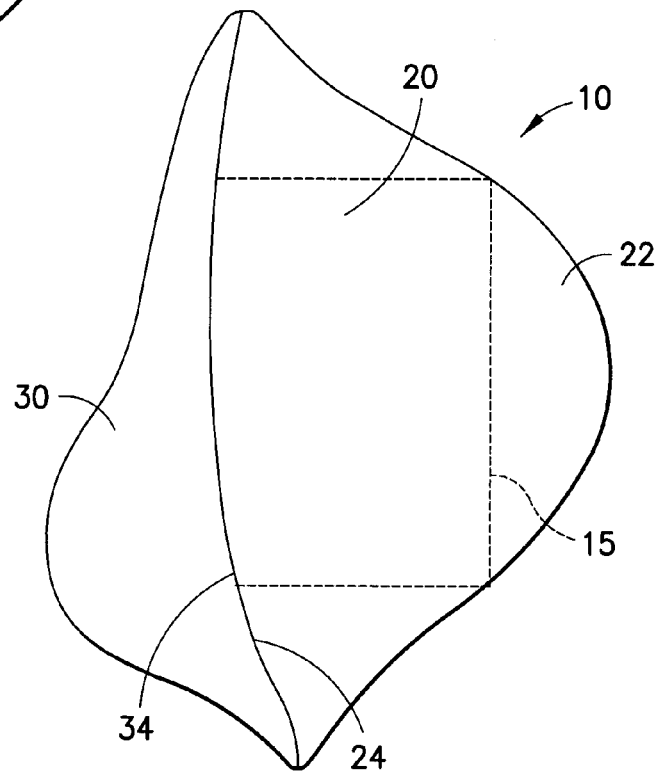
FIG. 6 is a side perspective view of the first embodiment with a laminated picture located therein.
Figure 7:
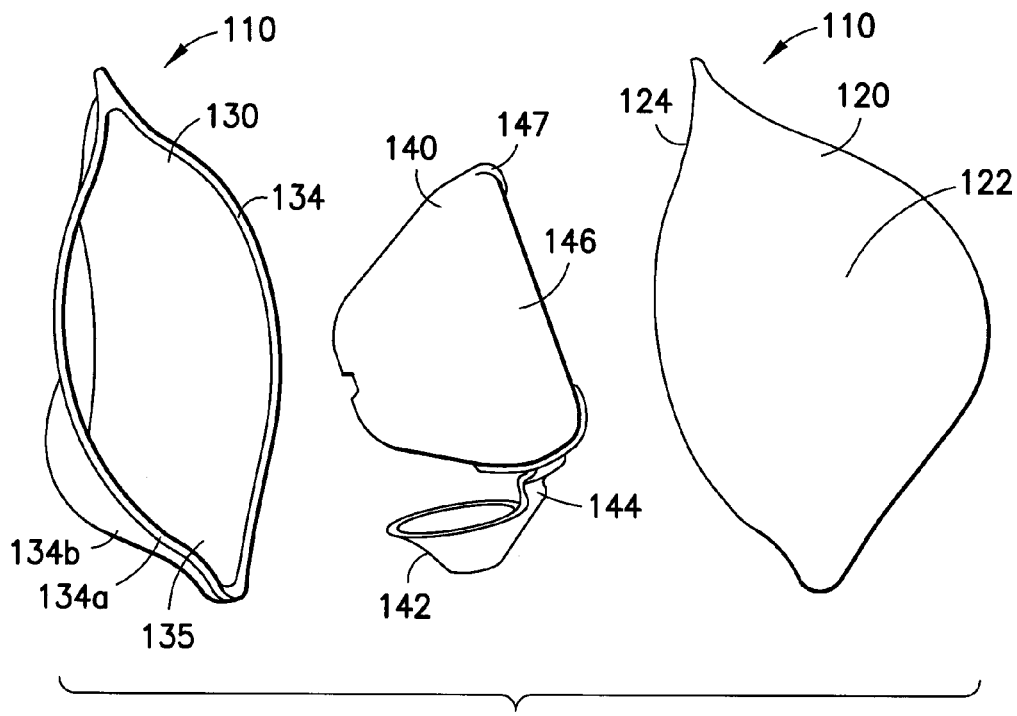
FIG. 7 is an exploded side perspective view of a second embodiment of a display device.
Figure 8:
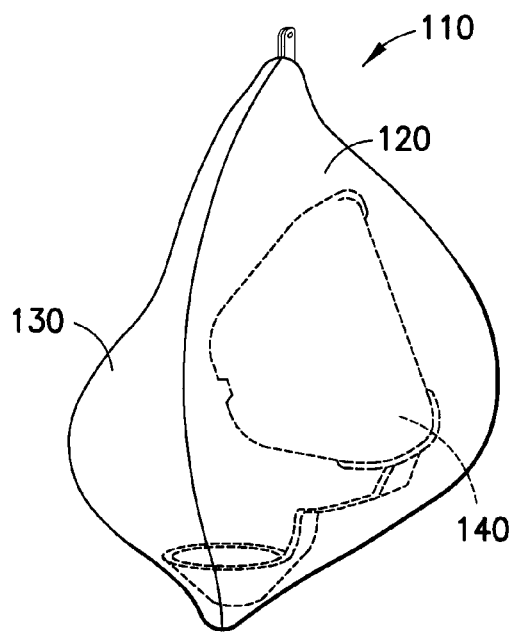
FIG. 8 is a side perspective view of the second embodiment.
Figure 9:
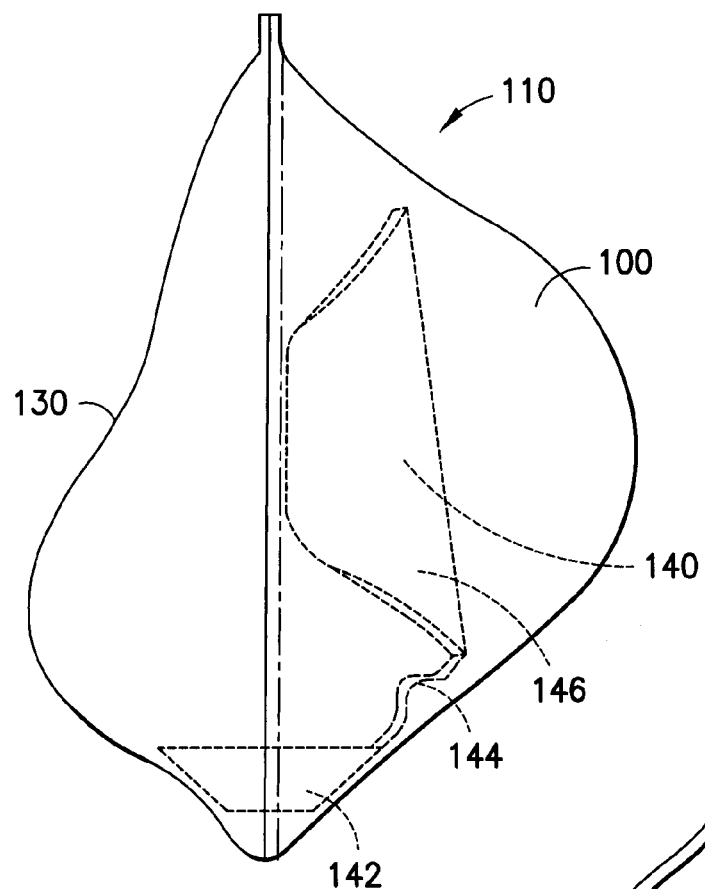
FIG. 9 is a side view of the second embodiment of FIG. 8.
Figure 10:
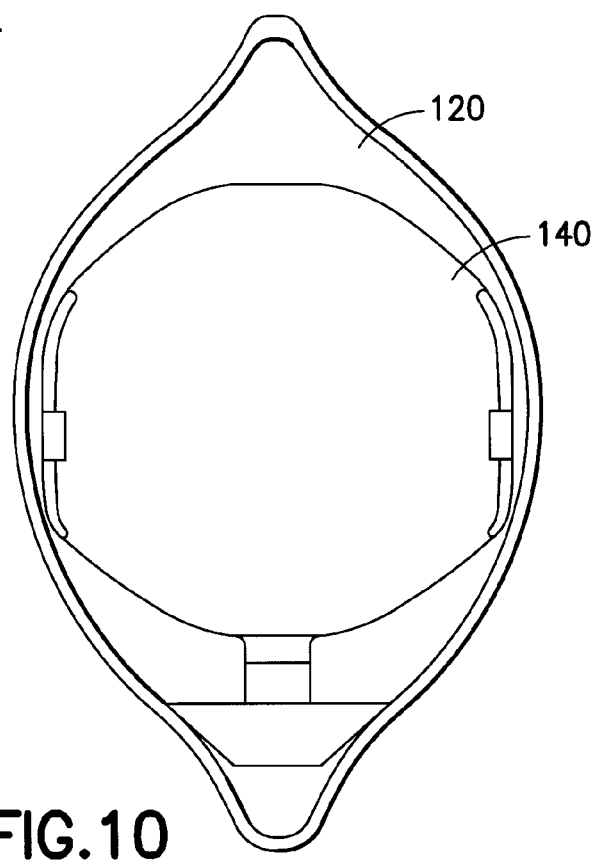
FIG. 10 is a front view of the second embodiment of FIG. 8.

A first embodiment of a keepsake ornamental display device 10 is seen in FIGS. 1-6. As shown, the device 10 is intended to safely store and displaying a printed ultrasound image 15 (FIGS. 2, 3, 6). The display device 10 includes a translucent hollow convex first member 20 with a preferably smooth outer surface 22 and inner surface 23 and mimics a pregnant belly. If desired, the smooth surface 22 may be interrupted by a central indent 25 or hole that mimics a belly-button. The indent or hole 25 may be adapted to receive a birthstone or plastic chip (not shown) with the color of an appropriate birthstone. The birthstone or plastic chip may be provided as part of a kit discussed below. The back of the hollow member 20 presents an edge 24. A second member 30 is provided to close the back of the convex member. The second member may take any of various shapes, but in the embodiment shown, the second member 30 has a closed portion shaped as the buttocks of a woman and an open front portion which presents an edge 34. Together, the first member and second member represent the midsection of a pregnant woman. The first member 20 is preferably sufficiently transparent to permit details of an ultrasound photograph contained in the first member 20 to be viewed by an unaided eye. The second member 30 is optionally more opaque than the first member. The edges 24, 34 of the first and second member may be adapted to snap together and/or to be glued together (FIGS. 1, 6).

In the first embodiment, the inside surface 23 of the convex first member 20 is provided with one or more tracks or flanges 36 which are adapted to receive the printed ultrasound image 15. As shown in FIGS. 2 and 3, two flanges 36 are provided. The flanges 36 are generally horizontal, parallel arcs which present a curved track. The flanges 36 preferably extend far enough off of the inner surface 23 so as to accommodate a laminated image. Thus, the ultrasound image 15 can be laminated, and the laminated picture can be slid into place and held in place by flange(s) 36; i.e., along the track. Alternatively, the second member 30 may be provided with a convex surface which extends inside the first member 20 and on which one or more flanges are provided to hold the photograph or laminated photograph in place.

In one embodiment, one or both of the first member 20 and second member 30 may be shaped and may be provided with slots (not shown) in line with the flanges or track so that a lamination of the photograph 15 can be inserted through the slots and along the track. In this manner, the first and second members 20, 30 can be preassembled so that they do not come apart.

In one embodiment, one or both of the first member 20 and second member 30 are provided with a tab (not shown) or a hole (not shown) at the top area of the device 10. Where a tab is provided, the tab is provided with a hole. In this manner, a hole is provided which permits the device 10 to be hung as discussed hereinafter.

Turning now to FIGS. 7-13 another embodiment of a keepsake ornamental display device 110 is seen. The embodiment of FIGS. 7-13 is similar in some ways to the embodiment of FIGS. 1-6, and like or similar parts are numbered with a like number which is 100 larger. Thus, device 110 is provided a translucent hollow convex first member 120 with a preferably smooth outer surface 122 and inner surface 123 and mimics a pregnant belly. If desired, the smooth surface 122 may be interrupted by a central indent or hole (not shown) that mimics a belly-button and which may be adapted to receive a birthstone or plastic chip (not shown) with the color of an appropriate birthstone. The back of the hollow member 120 presents an edge 124 with an outer lip and an inner stop. A second member 130 is provided to close the back of the convex member. The second member may take any of various shapes, but in the embodiment shown, the second member 130 has a closed portion (with outer surface 132 and inner surface 133) shaped as the buttocks of a woman and an open front portion which presents an edge 134 with an inner lip 134a and an outer stop 134b which mate with the outer lip and inner stop of edge 124 of the outer lip. Together, the first member and second member represent the midsection of a pregnant woman. The first member 120 is preferably sufficiently transparent to permit details of an ultrasound photograph contained in the first member 120 to be viewed by an unaided eye. The second member 130 is optionally more opaque than the first member. The edges 124, 134 of the first and second member are preferably adapted to snap together and/or to be glued together. In the embodiment of FIGS. 7-12, a third member 140 is also provided to sit between the first and second members and to capture and/or support the laminated printed ultrasound image 115. More particularly, the third member 140 is provided with a centering cup 142, an arm 144 which extends upward and forward of the centering cup 140, and a support surface 146 attached to the arm 144 for holding and supporting the photograph. The cup 142, arm 144 and support surface 146 may be integrally formed, or may constitute two or more pieces which are glued, sonically welded, or otherwise attached to each other. Support surface 146 as shown with a convex curvature so as to present the photograph close to the inner surface 123 of the first member 120, and tapers on each side as it extends backward toward the second member 130. The support surface 146 is also preferably provided with a lip or flange 147 extending around at least a portion of the periphery of the third member 140. The lip 147 is intended to help hold a photograph (e.g., a laminated ultrasound photograph such as photograph 15 of the first embodiment) in place. The support surface 146 of the third member 140 is preferably shaped such that it is in contact or nearly in contact (as seen in FIG. 13) with the inner surface 123 of the first member 120 along some or much of its length. The centering cup 142 is shown to be formed as a hollow frusto-conical member which is adapted to sit down in the bottom area of the first and second members 120, 130. The centering cup 142 may be provided with a side hole 148 (FIG. 13) to accommodate a post 135 extending from the inside of the second member 130. In this manner, the centering cup 142 will be securely held in place.

In the embodiment of FIGS. 7-13, both the first member 120 and the second member 130 are provided at their top ends with tabs 128, 138 which are aligned and define a through-hole. As discussed hereinafter, this permits the display device to be hung as part of an assembly. Also, in the embodiment of FIGS. 7-13, the edges 124, 134 of the first and second members may be arranged with steps, tongues, grooves, or otherwise (e.g., lips and stops), to expedite mating of the members. As shown best in FIGS. 12 and 13, in the embodiment of FIGS. 7-13, the bottom 129 of first member 120 is provided as a solid finger with a horizontal inner surface which accommodates the bottom of the centering cup 142 as well as the bottom edge of the second member 130.

The keepsake display devices 10, 110 are preferably relatively small, e.g., less than six inches high, less than four inches wide, and less than five inches deep, and accommodate a standard printed ultrasound of 3.75 inches by 3 inches. In one embodiment, the display device 110 is approximately 5.5 inches high, approximately 3.5 inches wide, and approximately 4.25 inches deep. In the case of device 110, the printed ultrasound photograph should be cut to match the support surface 146. The display devices 10, 110 are preferably made out of moldable plastic. The first member is preferably made out of a clear moldable plastic such as, by way of example only, acrylic, polycarbonate, or polystyrene. In one embodiment, the second and/or third members are made out of the same material as the first member. In another embodiment, the second and/or third members are made out of a more opaque moldable plastic such as, by way of example only, polypropylene, polyethylene, or polyvinyl chloride. Because the display device has a desired outer shape, it also preferably has room to store other small keepsake items including, for example, a lock of baby hair.

Figure 14:
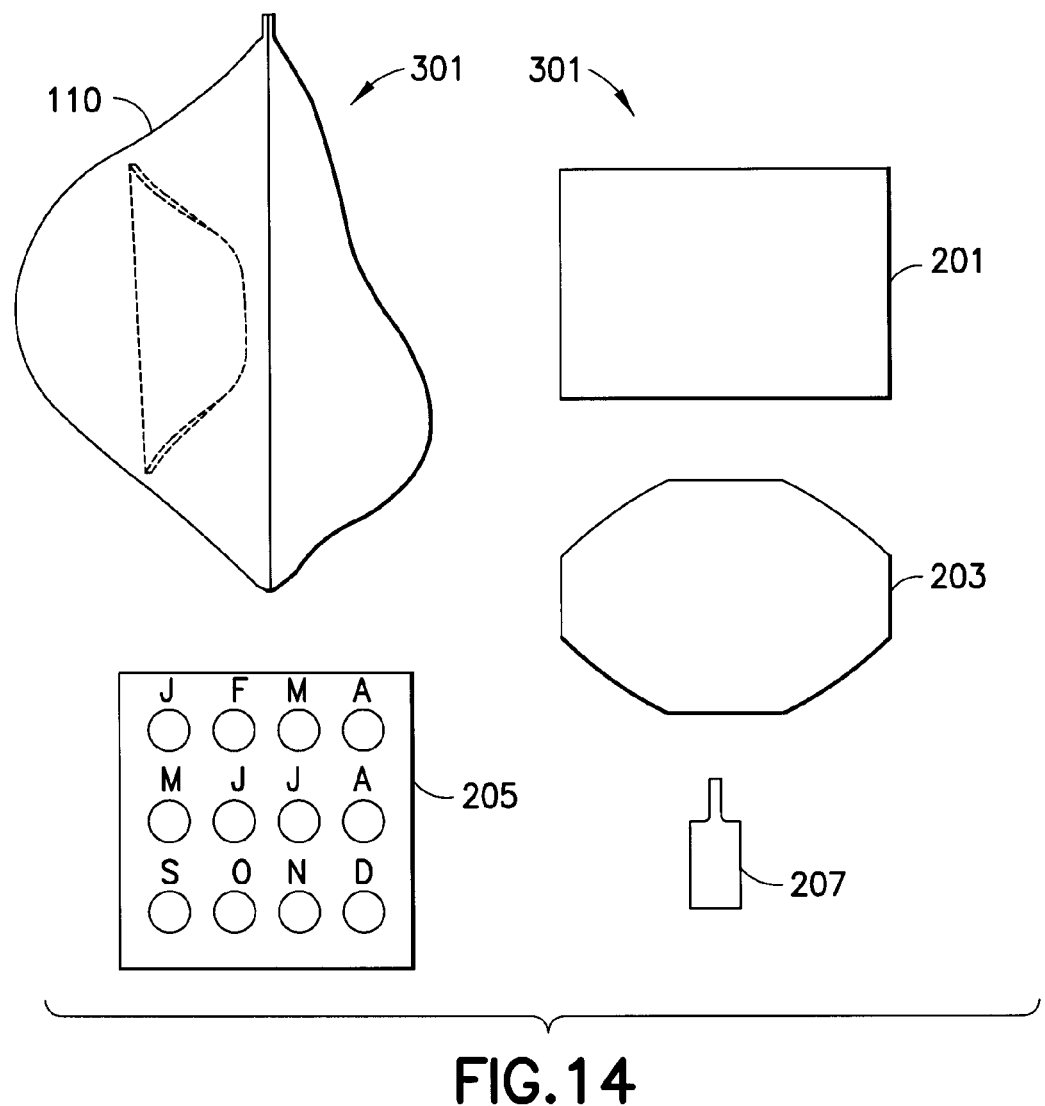
FIG. 14 is a schematic of various kit elements.

In one embodiment, a kit includes a display device 10 or 110 and a lamination member 201 seen in FIG. 14. The printed ultrasound image 15 can be placed inside the lamination member to form a laminated structure that can be received by the display device 10 or 110. The lamination member 201 can take different shapes depending upon the display device. For example, for display device 10, the lamination member 201 can be rectangular, and for display device 110, the lamination member 201 can take the shape of the support face 146 (i.e., generally oval). In addition, a template 203 for expediting cutting of the printed ultrasound image 15 (and lamination) can also be provided as part of the kit. If desired, scissors (not shown) may also be provided. Further, a birthstone, set of birthstones, or one or more plastic chips 205 with the colors of the various birthstones may be included as part of the kit. Glue 207 for attaching the birthstones to the display device and/or for attaching pieces of the display device to each other may also be provided. For purposes herein, the term "glue" is intended to encompass any type of adhesive or bonding agent.

Figure 15:
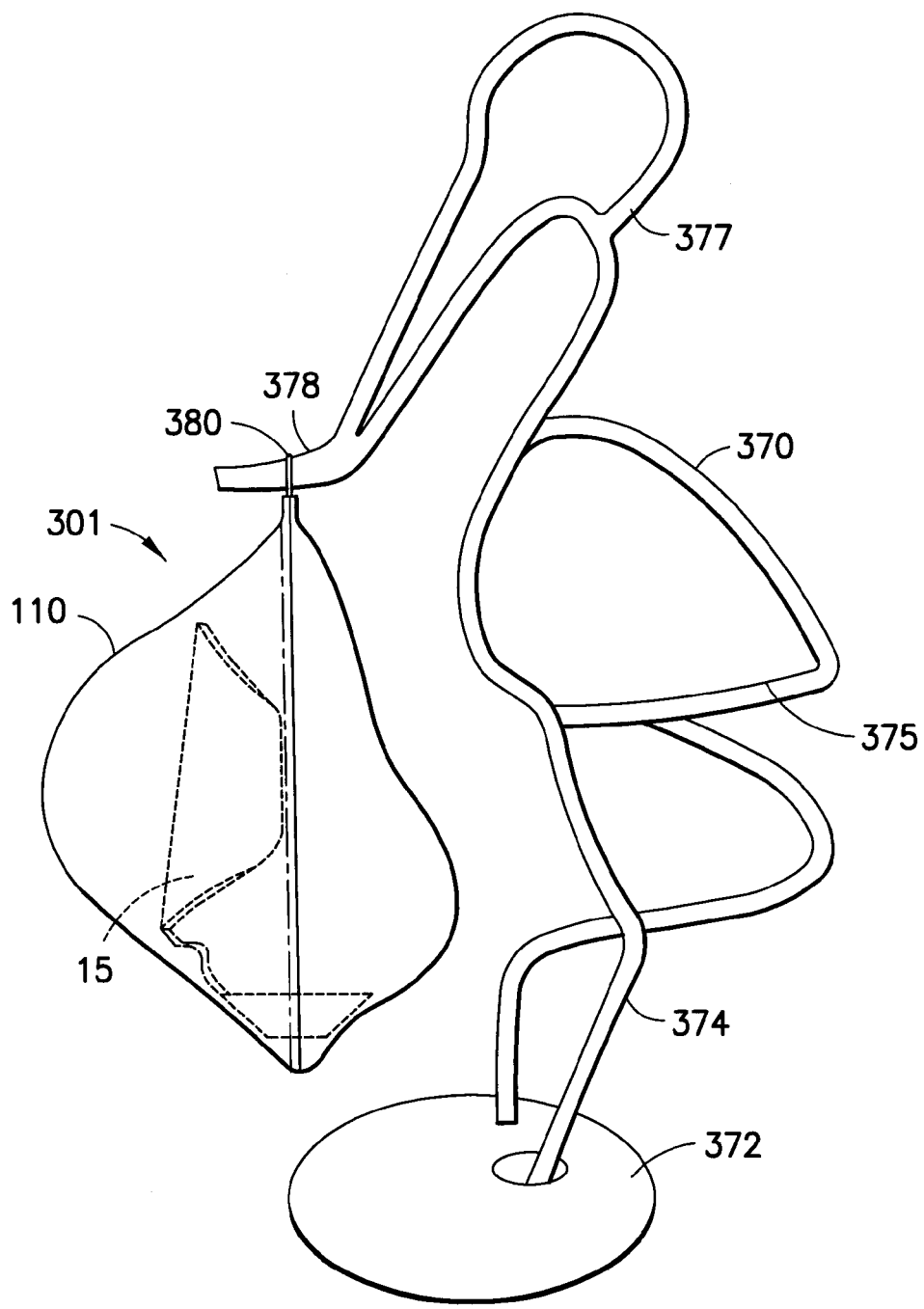
FIG. 15 is a schematic view of an assembly including a display device and a stand.

Turning to FIG. 15, according to another aspect of the invention, the display device 10, 110 may be used as part of an assembly 301 that further includes a figurine 375. The figurine 370 should have a stand and a body and means for holding the display device off of a support surface on which the stand sits. More particularly, in one embodiment, a figurine 370 is a wire sculpture resembling a stork is provided to hold the display device. The figurine 370 has a stand 372, at least one leg 374 attached to the stand, a wire body 375 extending from the leg, and a head 377 extending from the body 375. The head 377 includes a generally horizontal beak 378 which is adapted to extend through an opening in the display device (e.g., through tabs 128, 138 of display device 110), or through a ring or hook 380 which is attached to or through the display device so as to hold the display device in a dangling position above the horizontal level of the stand 372. Alternatively, a ribbon or other attachment device can be used to extend through the ring attached to the display device or through the hole(s) in the display device in order to attach the display device to figurine.

There have been described and illustrated herein several embodiments of a display device, a kit including the display device, and an assembly including the display device. While particular embodiments of the invention have been described, it is not intended that the invention be limited thereto, as it is intended that the invention be as broad in scope as the art will allow and that the specification be read likewise. Thus, while particular plastic materials have been disclosed in forming the display device, it will be appreciated that other materials such as glass, metal, etc., may be used as well. In addition, while particular sizes have been disclosed, it will be understood that other sizes can be used. Also, while a particular figurine has been described as part of the assembly, it will be appreciated that other figurines could be utilized. It will therefore be appreciated by those skilled in the art that yet other modifications could be made to the provided invention without deviating from its spirit and scope as claimed.

What is claimed is:

1. A keepsake display device, comprising:
   a) a substantially transparent non-spherical hollow first member with a substantially closed smooth mostly convex outer surface having a first apex, said hollow first member defining a back opening along a plane;
   b) a non-spherical second member coupled to said first member and having a substantially closed smooth outer surface closing said back opening, thereby defining a substantially closed outer surface for said device and a space within said device, said closed smooth outer surface of second member having a convex portion defining a second apex with said second apex displaced below said first apex relative to said plane, and said closed outer surface of said second member having at least one concave portion;
   c) an ultrasound image of a fetus; and
   d) a display element located within said space and adapted to receive said printed ultrasound image and to display said printed ultrasound image through the outer surface of said first member, wherein
      said hollow first member is shaped to mimic a pregnant belly, and said second member is shaped to mimic a woman's buttocks with said concave portion representing a small of a woman's back, such that said first member and second member together represent the midsection of a pregnant woman with said ultrasound image of a fetus held therein,
      said first member has a first bottom area with a first inside wall surface, said second member has a second bottom area with a second inside wall surface, and said first bottom area and second bottom area taper in width,
      said display element includes a centering element located held between said first and second inside wall surfaces, an arm extending upward and forward of said centering element, and a support surface attached to said arm, said support surface adapted to hold and support said printed ultrasound image in said space within said device, and
      said support surface has a convex curvature facing an inner surface of said first member, and said support surface tapers as it extends backward toward said second member, and wherein said convex curvature of said support surface permits said support surface to fit within said non-spherical hollow first member.

2. A display device according to claim 1, wherein:
said substantially closed smooth outer surface defines a central indent or hole that mimics the naval of the pregnant woman.

3. A display device according to claim 1, wherein:
said support surface is provided with a lip extending around at least a portion of a periphery of said support surface and adapted to hold said printed ultrasound image in place.

4. A display device according to claim 1, wherein:
said printed ultrasound image is a laminated printed ultrasound image.

5. A kit, comprising the display device of claim 2, and further comprising either a birthstone, a set of birthstones, a plastic chip resembling a birthstone, or a set of plastic chips resembling a set of birthstones.

6. A kit according to claim 5, further comprising a template adapted to expedite cutting of said ultrasound image, and glue.

7. An assembly comprising the display device of claim 1 and a figurine having a stand, said figurine adapted to hold said display device in its entirety above a horizontal level of said stand.

8. An assembly comprising the display device of claim 2 and a figurine in the shape of a stork with a beak, said figurine having a stand, and said display device either defining an opening through which said beak can extend or said display device coupled to a ring or hook through which said beak can extend such that said figurine holds said display device in its entirety above a horizontal level of said stand.

* * * * *